United States Patent [19]

Zak

[11] 4,075,128
[45] Feb. 21, 1978

[54] PREPARATION OF METHYL ETHYL KETONE

[75] Inventor: Thomas Stephen Zak, Springfield, Pa.

[73] Assignee: Atlantic Richfield Company, Los Angeles, Calif.

[21] Appl. No.: 745,504

[22] Filed: Nov. 26, 1976

[51] Int. Cl.$^2$ .................. B01J 23/16; C07C 45/00
[52] U.S. Cl. ............................ 252/475; 260/596
[58] Field of Search .............. 260/596; 252/465, 475

[56] References Cited

U.S. PATENT DOCUMENTS

| | | | |
|---|---|---|---|
| 2,472,493 | 6/1949 | Schneider et al. | 260/596 |
| 2,474,440 | 6/1949 | Smith et al. | 260/596 |
| 2,701,264 | 2/1955 | Deahl et al. | 260/596 |
| 2,891,095 | 6/1959 | Opitz et al. | 260/596 |
| 3,894,963 | 7/1975 | Gardes et al. | 252/465 |

FOREIGN PATENT DOCUMENTS

| | | | |
|---|---|---|---|
| 2,627,230 | 12/1976 | Germany | 260/596 |
| 624,035 | 5/1949 | United Kingdom | 260/596 |

Primary Examiner—James O. Thomas, Jr.
Assistant Examiner—James H. Reamer
Attorney, Agent, or Firm—John R. Ewbank

[57] ABSTRACT

Vapors of secondary butyl alcohol are directed through a bed of heat-treated pellets of compressed brass powder to provide methyl ethyl ketone. In preparing the pellets from powder, more than half of the brass powder has a particle size less than 44 microns. Less than 1% of the powder is larger than 60 mesh, that is, larger than 250 microns. A significant portion of the powder has a size range between 60 mesh and 325 mesh, i.e. smaller than 250 microns, but larger than 44 microns. The powder is desirably mixed with about 0.1 to about 1% lubricant such as stearic acid or zinc stearate. The lubricant coated powder is compressed, generally into a cylindrical pellet having a height about equal to its diameter. The pellets may desirably be about one fourth inch in diameter and about one fourth inch long. The compressed pellets are subjected to heat treatment conditions corresponding to a temperature within a range from about 900° F. to about 1000° F. for about one hour. Such temperature range can be expressed as about 480° C. to about 540° C. Without the controlled heat treatment, pellets have inadequate attrition resistance and compressive strength. When the heat treatment is at a temperature or time which are excessive, then the surface area and pore volume of the activated pellet is reduced enough to impair the advantageous activity of the catalyst.

2 Claims, No Drawings

PREPARATION OF METHYL ETHYL KETONE

FIELD OF INVENTION

This invention relates to heat activated catalyst pellets derived from compressed powdered brass and to a method of preparing methyl ethyl ketone using such catalyst pellets.

PRIOR ART

Heretofore one of the industrial methods for preparing methyl ethyl ketone has involved directing hot vapors of secondary butyl alcohol through a zone containing an appropriate dehydrogenation catalyst. The literature discloses many varieties of dehydrogenation catalyst effective for this or similar reactions. Some commercial production of methyl ethyl ketone has utilized blocks of cast brass as the catalyst. Because the cast brass blocks have high selectivity and longevity, there have been advantages to using the brass catalyst even though brass is not as active a dehydrogenation catalyst as certain other catalysts which have been proposed for this reaction.

A method for evaluating the pore volume of a block of cast brass makes use of a light machine oil as a pore-filler. The sample is immersed in the light machine oil which is then subjected to a vacuum to facilitate interchange of the oil with the air already in the pores. The pore volume is calculated on the basis of the weight of the oil thus drawn into the pores. The pore volume of a sample of a commercially used cast brass catalyst was 22 cc per kilogram or 0.022 cc per gram.

Notwithstanding the various investigations of the synthesis of methyl ethyl ketone by the dehydrogenation of secondary butyl alcohol, some technologists continued to be dissatisfied with various proposals for alternatives to the cast brass catalyst.

SUMMARY OF THE INVENTION

In accordance with the present invention, secondary butyl alcohol is directed through a bed of pellets of compressed brass powder to provide methyl ethyl ketone and hydrogen. The pellets are prepared by compressing a lubricated powder, more than half of the weight of the powder having a particle size less than about 44 microns. Less than 1% of the powder is larger than 250 microns. A significant portion of the powder has a size range between about 44 microns and about 250 microns. Such lubricated brass powder can be compressed into pellets having sufficient strength to be transferred to the zone for the heat treatment. The pellets are heat treated at a temperature within a range from about 900° F. to about 1000° F. for about one hour.

The nature of the invention is further clarified by reference to a plurality of examples.

EXAMPLE 1.

A brass powder is prepared by spraying a molten brass. The brass powder has an analysis as follows:

|  |  | wt. % |
| --- | --- | --- |
| Copper |  | 53.9 |
| Zinc |  | 45.2 |
| Manganese |  | 0.021 |
| Iron |  | 0.000076 |
| Magnesium | less than | 0.000005 |
| Aluminum | less than | 0.000004 |
| Silver | less than | 0.000040 |
| Lead | less than | 0.10 |

The particle size distribution for the brass powder was as follows:

| Mesh Size | Particle Size Microns | % of Total |
| --- | --- | --- |
| 60 | 250 | 0.3 |
| +100 | 149 | 0.03 |
| +200 | 74 | 26.6 |
| +325 | 44 | 22.1 |
| −325 | less than 44 | 51.0 |
|  |  | 100.0 |

A sample of stearic acid was dissolved in acetone and impregnated into the powder to provide a lubricated powder containing 0.5% stearic acid.

The lubricated powder was fed to a pelleting machine for formation of cylindrical pellets. The cylindrical pellets were transferred to a heat treating furnace and activated at a temperature maintained between 900° F. and 1000° F. for about one hour. The pellets were cooled and subjected to various tests, including attrition tests and surface area tests. In the attrition test, 10 pellets were shaken sideways in a 4 dram bottle using a shaking frequency of 300 cycles per minute for three minutes. The amount of loss of the on-size pellets was designated as the attrition loss.

In a series of tests to determine the optimum activating conditions, the effect of heat treatment upon pore volume was noted. Any activation involving a temperature of at least 800° F. appeared to be effective in decreasing the attrition to a manageable level. The results of various heat treatments of the raw pellets are shown in the following table:

| Catalyst Pretreatment | Pore Volume | % Attrition Loss |
| --- | --- | --- |
| None | 0.042 | 32 |
| 800° F. for one hour | 0.044 | 1.5 |
| 900° F. for one hour | 0.047 | 0.1 |
| 1000° F. for one hour | 0.042 | 0.1 |
| 1200° F. for 45 min. | 0.024 | 0.1 |
| 1400° F. for 45 min. | 0.010 | 0.1 |
| 1600° F. for 45 min. | 0.003 | 0.1 |

In order to avoid excessive loss of pore volume, while still achieving an acceptable degree of attrition resistance, the heat-treatment should correspond to the effect of a treatment at a temperature between 900° F. and 1000° F. for 1 hour.

Pellets which had been heat-treated at about 950° F. for one hour were placed in a reactor and a nitrogen stream was directed through the catalyst bed while maintaining a pressure of about 150 psig while heating the catalyst bed to a temperature of 750° F. After the pressure was stabilized at 150 psig and the temperature was stabilized at about 750° F., the secondary butyl alcohol reactant was introduced as a vapor. The catalyst bed served as a dehydrogenation catalyst so that the secondary butyl alcohol was converted to methyl ethyl ketone at a very high selectivity and with a conversion of about 75%. A condenser was employed for cooling the reactant stream and for condensing a liquid product consisting predominantly of methyl ethyl ketone and secondary butyl alcohol. The liquid product, condensed under pressure, was subjected to distillation at atmospheric pressure for the recovery of the methyl ethyl ketone product and for the recovery of the recycled stream of secondary butyl alcohol. Heavy products can form as byproducts from the reaction, but the quantity formed using said brass catalyst of the present invention was only a tiny fraction of the methyl ethyl ketone produced.

In a control preparation, the pelleting pressure was increased to increase the density of the pellet. After heat treatment at 950° F. for one hour, and cooling, the pellet had a pore volume of 0.19 cc/gm and a density providing 1.32 g per pellet, or about 19% heavier than the 1.11 g per pellet of the desired catalyst. The high density pellets had a pore volume of only 0.019 cc/g, or 54% less than the 0.042 cc/g of the desired catalyst.

By a series of tests it is established that the pore volume of a satisfactory catalyst should be within a range from about 0.038 to about 0.046 cc/gm or 0.042 ± 0.004 cc/g. Such pore volume is associated with pellets having a density of from about 5 to about 6 g/cc or about 5.5 ± 0.5 g/cc. In said control preparation in which the one-fourth inch by one-fourth inch cylindrical pellet weighed 1.32 g and had a density of 6.57 g/cc (well outside the range required by the present invention, but far below the about 8.2 g/cc of brass alloy containing 45% zinc), there was only 33% conversion when secondary butanol was dehydrogenated at a space velocity of about 1 liquid volume per volume of catalyst per hour to methyl ethyl ketone at 700° F. and at about 125 psig. Such 33% conversion is significantly inferior to the 60% conversion at 700° F. and about 125 psig using the catalyst of the present invention. As previously noted, a conversion of 75% was attained using the catalyst of the present invention at 750° F. and 125 psig.

When cast brass blocks of the type commercially employed as a catalyst for MEK synthesis were employed as a control for dehydrogenating secondary butyl alcohol to methyl ethyl ketone at 750° F. and 125 psig at the standard space rate (LHSV about one) used throughout the tests herein, the conversion was only 45%. Thus the 75% conversion of the pelletted brass catalyst represents a 67% improvement over a commercially employed catalyst while still providing the high selectivity desired in this reaction. Heretofore attempts to employ catalysts known to be more active as dehydrogenation catalysts than cast brass blocks have produced excessive by products. Over a period of many years, many tons of methyl ethyl ketone have been produced using cast brass blocks as the catalyst bed. Partly because of the remarkable stability of the catalyst for industrial use over a period of many years, there was resistance to change. The present invention preserves advantages selectivity while providing a 67% improvement in activity and conversion.

Various modifications of the invention are possible without departing from the scope of the appended claims.

I claim:

1. In the method of preparing methyl ethyl ketone by directing the vapors of secondary butyl alcohol through a catalytic dehydrogenation zone, the improvement which consists essentially of employing in said process a catalyst formed by:

preparing a brass powder having more than 50% of the particles having a particle size less than about 44 microns, less than 1% having a particle size larger than 250 microns, and the balance of the particles having a particle size from about 44 to about 250 microns, compressing said brass powder into pellets each pellet having a density between about 5 and 6 grams per cubic centimeter, heat treating a bed of pellets at conditions corresponding to treatment at about 950° F., ±50° F. for about one hour to provide activated pellets having a pore volume within a range from about 0.038 to about 0.046 cc per gram, employing said activated pellets for said dehydrogenation of secondary butyl alcohol said dihydrogenation being at a pressure of from about 100 to about 150 psig at a temperature of from about 700° F. to about 750° F. at a liquid hourly space rate of about one.

2. The method of preparing catalyst pellets which method consists essentially of:

preparing a brass powder having more than 50% of the particles having a particle size less than about 44 microns, less than 1% having a particle size larger than 250 microns, and the balance of the particles having a particle size from about 44 to about 250 microns, compressing said brass powder into pellets, each pellet having a density between about 5 and 6 grams per cubic centimeter, heat treating a bed of pellets at conditions corresponding to treatment at about 950° F., ±50° F. for about 1 hour to provide activated pellets having a pore volume within a range from about 0.038 to about 0.046 cc per gram.

* * * * *